United States Patent [19]

Kaplan

[11] 4,051,186

[45] Sept. 27, 1977

[54] AMINO-PROPRANOLOL

[75] Inventor: Nathan O. Kaplan, La Jolla, Calif.

[73] Assignee: The Regents of the University of California, Berkeley, Calif.

[21] Appl. No.: 652,951

[22] Filed: Jan. 28, 1976

Related U.S. Application Data

[60] Division of Ser. No. 523,618, Nov. 13, 1974, abandoned, and a continuation-in-part of Ser. No. 481,282, June 20, 1974, Pat. No. 3,950,422.

[51] Int. Cl.$^2$ .............................................. C07C 93/06
[52] U.S. Cl. ................................ 260/570.7; 260/112.7; 260/285; 260/293.54; 260/319.1; 260/397.5; 260/570.5 C; 260/570.6; 424/316; 424/330; 548/300; 560/19
[58] Field of Search ............ 260/570.7, 501.17, 501.18

[56] References Cited

U.S. PATENT DOCUMENTS

| 3,337,628 | 8/1967 | Crowther et al. | 260/570.7 |
|---|---|---|---|
| 3,410,901 | 11/1968 | Kunz et al. | 260/570.6 |
| 3,432,545 | 3/1969 | Howe | 260/501.17 |
| Re. 27,822 | 11/1973 | Koppe et al. | 260/570.7 X |

*Primary Examiner*—Robert V. Hines
*Attorney, Agent, or Firm*—Samuel L. Welt; Jon S. Saxe; George M. Gould

[57] ABSTRACT

Biologically active substances having labile aryl groups can be converted to the corresponding aryl amine derivatives. The biologically active substances are reacted with a diazonium compound which optionally can be linked to a solid, inorganic carrier such as porous glass beads for ease of purification. The diazo reaction product is then reductively cleaved with a chemical reducing agent such as with hydrosulfite to yield the desired amine derivative. A preferred class of biologically active substances used herein is the catecholamines.

1 Claim, No Drawings

AMINO-PROPRANOLOL

RELATED APPLICATIONS

This is a division of application Ser. No. 523,618 filed Nov. 13, 1974 and now abandoned, and a continuation-in-part of copending application Ser. No. 481,282, filed June 20, 1974 and now U.S. Pat. No. 3,950,422.

BACKGROUND OF THE INVENTION

The compound 6-aminonorepinephrine .2HBr is disclosed in a paper by Mannich and Berger, Archiv. Pharmazie, 277, 117 (1939). It was prepared by catalytic hydrogenation of the keto moiety of the corresponding 6-amino acetophenone compound.

Immobilization of catecholamines on aryl or alkyl amine glass beads via diazotization has been described by Venter et al. in Proc. Nat. Acad. Sci., U.S.A., 69, 1141 (1972) and in Proc. Nat. Acad. Scie., U.S.A., 70, 1214 (1973).

Regeneration of solid carrier supports which have been linked to a protein material such as an enzyme, through a diazo linkage, using sodium dithionite is disclosed in German Pat. No. 2,336,428. After the regeneration, the solid carrier contains an amino group which can be used to recouple with fresh protein.

DESCRIPTION OF THE INVENTION

The present invention relates to a process for preparing aryl amine derivatives of biologically active substances which substances initially contain a labile aryl group. It is already known in the art that biologically active substances can be bonded to glass beads. Such bonding is accomplished by converting the glass beads to the aryl amine derivatives, diazotizing said derivative and then reacting the diazonium salt with the labile aryl group of the biologically active substance.

In accordance with the process of the instant invention, it has been discovered that diazonium derivatives of biologically active substances can be reductively cleaved with a chemical reducing agent in such a manner that an amino group is introduced into the aryl moiety of the biologically active substances at the site where the diazonium coupling took place. It should be noted that the instant process is not limited to the use of diazonium salts bonded to glass surfaces but may also employ soluble diazonium salts obtained most preferably from aromatic amines such as for example from p-aminobenzoic acid, amide derivatives thereof or p-nitroaniline.

Suitable biologically active substances having labile aryl groups for use in accordance with the process of the present invention include the following representative examples:

a. catecholamines — such as epinephrine, norepinephrine, ethylnorepinephrine, dopamine and the like.

b. adrenergic agents — such as isoproteronol, ephetonal, propranolol, ephedrine and the like;

c. local anesthetics — such as procaine, benzocaine, procaine amide, butacaine, benoxinate, nasacaine, proparacaine, tetracaine, propoxycaine, lidocaine, cyclomethycaine, mepioacaine, hexylcaine, deperodon, dibucaine, and the like.

d. anti-infective agents — such as semi-synthetic penicillins, e.g., ampicillin, phenoxymethyl penicillin, phenethicillin, cloxacillin, methicillin, nafcillin, oxacillin and the like, tetracyclines, e.g., demethyl-chlortetracycline, rolitetracycline, chlortetracycline and the like, sulfonamides such as sulfisoxazole, sulfadimethoxine, sulfamethoxazoles, sulfamethizole, sulfisomidine, sulfachlorpyridazine, sulfaethidole, sulfamethoxypyridazine and the like;

e. antimalarial agents — such as quinine, quinacrine, amodiaquine, chloroquine, hydroxychloroquine, primaquine and the like;

f. anthelintics — such as dithiazanine iodide, pyrvinium pamoate, and the like;

g. anticonvulsants — such as diphenylhydantoin, ethotoin, methsuximide and the like;

h. anorexiants — such as amphetamine, methamphetamine, benzphetamine, chlorphentermine, diethylpropion, phendimetrazine, phentermine, and the like;

i. antidepressants — such as amitriptyline, desipramine, imipramine, isocarboxazid, nialamide, nortriptyline, phenelzine, tranylcypromine and the like;

j. antipsychotic agents — such as acetophenazine, carphenazine, chlorprothixene, fluphenazine, perphenazine, prochlorperazine, thiopropazate, thioridazine, trifluoperazine, triflupromazine and the like;

k. antianxiety agents — such as benactyzine, baclizine, chlorodiazepoxide, chlormezanone, diazepam, hydroxyphenamate, hydroxyzine, mephenoxalone, oxazepam, phenazlycodol and the like.

l. skeletal muscle relaxants — such as chlorphenesin carbamate, chloroxazone, metaxalone, methocarbamol, styramate and the like;

m. sedatives - hypnotics — such as flurazepam, methaqualone and the like;

n. analgesics — such a morphine, codeine, heroin, hydromorphone, oxymorphone, anileridine, phenazocine, indomethacin, piminodine, ethoheptazine, oxyphenbutazone, phenyramidol, propoxyphene and the like;

o. narcotic antagonists - such as nalorphine, methadone, levallorphan, alphaprodine, levorphanol, and the like;

p. analeptics — such as methylphenidate, doxapram, ethamivan and the like;

q. antihisamines — such as phenindamine, diphenhydramine, promethazine brompheniramine, cyproheptadine, dexbrompheniramine, dischloropheniramine, dimethindene, methdibazine, trimepreazine, triprolidine and the like;

r. antiemetics — such as thiethylperazine, trimethobenzamide and the like;

s. antitussives — such as dextromethorphan, benzonatate, chlophedianol, dimethoxanate, pipazethate and the like;

t. vasopressors — such as angiotensin amide, phenylephrine, mephentermine, and the like;

u. antihypertensives — such as desperidine, methyldopa, pargyline, syrosingopine, and the like;

v. diuretics — such as bendroflumethiazide, benzthiazide, chlorothiazide, chlorthalidone, cyclothiazide, hydrochlorothiazide, hydroflumethiazide, methyclothiazide, polythiazide, quinethazone, trichloromethiazide, furosemide and the like;

w. peripheral vasodilators — such as isoxsuprine, nylidrin and the like;

x. anticoagulants — such as acenocoumarol, warfarin, anisindione, phenprocoumon and the like;

y. antiparkinsonism agents — such as dopa, biperiden, chlorphenoxamine, orphenadrine and the like;

z. estrogens — such as ethinyl estradiol, mestranol, estradiol, estrone, estriol and the like;

aa. hypoglycemic agents — such as acetohexamide, chlorpropamide, phenformin, tolazamide, tolbutamide and the like;

bb. antispasmodics — such as glycopyrrolate, hexocyclium, methylsulfate, isopropamide, methixene, oxyphencyclimine, valethamate, diphenoxylate, fluorantyrone, and the like;

cc. enzymes — such as chymotrypsin, streptokinase, alpha amylase, fibrinolysin, hyaluronidase, pancrelipase, penicillinase, and the like;

dd. immunologic agents — such as antigenic substances, e.g., toxoids and vaccines for diphtheria, tetanus, pertussis, smallpox. poliomyelitus, measles, rabies, influenza, typhoid and the like or antibodies;

ee. hormones — such as insulin, thyroxine, tri-iodothyronine, thyroblobuline, papain, ficin, pepsin, trypsin, chymotrypsin, brometin, keratinase, cellulase, maltase pectinase, angiotensin, ACTH and the like.

ff. natural agents — such as histamine, serotonin and the like.

The site of electrophilic attack by the diazonium compound on the aryl group or groups of the biologically active substances will depend on the nature of the existing substituents on these groups. Position directing effects of various substituents on aryl groups towards electrophilic attack are well known in the art. See for example in this regard Gould, Mechanism and Structure in Organic Chemistry, pp. 220–227 (1959).

Suitable inorganic carrier materials which may be utilized in the practice of the present invention include those inorganic materials having available oxide and/or hydroxide groups. These materials are substantially water insoluble and are either weak acids or weak bases. They may also be classified in terms of chemical composition as siliceous materials or non-siliceous metal oxides. Of the siliceous materials, a preferred carrier is porous glass either in particulate form, e.g., as beads having average diameters in the range of about 1 to 300 microns or as an integral piece such as a disc. Glass has the advantage in that it is dimensionally stable and that it can be thoroughly cleaned to remove contaminants as, for example, by sterilization. Porous glass useful as a carrier is readily available and sold commercially by Corning Glass Works as Code GZO-2930 beads or Code 7930 porous glass.

Other siliceous inorganic carriers which can also be used include colloidal silica (commercially available under the trademark CAB-O-SIL), wollastonite (a naturally occurring calcium silicate) dried silica gel and bentonite. Representative non-siliceous metal oxides include alumina and hydroxyapatite.

The inorganic carrier material is converted into the corresponding alkyl amine derivative by using procedures well known in the art. See, for example, Weetall, Science, 166, 615-617 (1969); Venter et al., Proc. Nat. Acad. Sci. U.S.A., 6, 1141–1145 (1972); and Venter et al., Proc. Nat., Acad. Sci. U.S.A., 70, 1214–1217 (1973).

The alkyl amine derivatized inorganic carrier materials is then treated with a p-nitroaroyl halide, most preferably p-nitrobenzoly chloride followed by chemical reduction with a reducing agent such as dithionite to form the desired aryl amine modified carrier material. The procedures for such conversion are known in the art as apparent from the references appearing immediately above.

Formation of the diazonium salt of aryl amine modified carrier material is carried out in a manner known per se. Diazotization is conveniently accomplished by treating the aryl amine with a slight excess of sodium nitrite in aqueous mineral acid, e.g., hydrochloric acid usually at a temperature in the range of about 0° to 4° C.

In a similar fashion, a diazonium salt of a p-aminoarylcarboxylic acid or an amide thereof, most preferably p-aminobenzoic acid, or p-nitroaniline can be prepared for that aspect of the invention where the diazonium compound is desired to be in a soluble form.

Coupling of the biologically active substance with either the soluble or insoluble diazonium compound is carried out by adding the diazonium compound or solution, which has been previously neutralized by addition of the requisite amount of sulfanic acid followed by washing with distilled $H_2O$ (or urea with the soluble drug), to a solution containing a slight excess of the biologically active substance. The coupling reaction is conducted at a temperature in the range of from about 0° to 4° C., most preferably at about 0° C. While aqueous systems are used whenever possible, it is within the scope of this disclosure to employ organic solvents in conjunction with those biologically active substances which have limited water solubility. Suitable organic solvents for this purpose include lower alkanols such as methanol or ethanol, ethers such as dioxane or tetrahydrofuran, dimethylformamide, dimethylacetamide, acetonitrile, acetone, dimethylsulfoxide and the like.

The resulting diazo coupled biologically active substance is than treated with a chemical reducing agent, most preferably an akali hydrosulfite such as sodium dithionite (commercially available from Matheson, Coleman and Bell).

The reduction is conveniently carried out at a temperature in the range of from about 0° to 4° C., although the temperature employed is not narrowly critical. Generally an excess of the chemical reducing agent is utilized.

The reduction procedure results in a cleavage of the diazo linkage thus producing an amino derivative of the biologically active substances with the amino group being situated on the labile aryl moiety at the site of the electrophilic diazonium substitution.

In this manner, the process of this invention provides a convenient general method for introducing amino groups into biologically active substances having labile aryl groups. Such process is particularly advantageous in that it is conducted at mild reaction conditions and thus will not adversely affect the biologically active substances. The instant process can be used to prepare known derivatives of biologically active substances, novel derivatives of biologically active substances or as a means to test the sites of activity on such biologically active substances. Thus, for example, the instant process was utilized with isoproterenol, epinephrine, dopamine and serotonin to produce the novel 6-amino derivatives of the aforesaid compounds. In general, the amino derivatives of the biologically active substances will have the same pharmacological activity spectrum as the parent substances but with enhanced duration of activity.

Thus, the novel catecholamines exhibited unexpectedly superior pharmacological properties over the corresponding des-6-amino compounds. For example, the known catecholamines when tested in standard in vitro systems such as ilium muscle strips or heart papillary muscles gave a duration of biological activity which rarely exceeded 30 minutes. In contrast, 6-amino-isoproterenol and 6-amino-epinephrine yielded effects equal in magnitude to the corresponding des-6-amino compound but the duration of action was substantially prolonged, producing effects for greater than 6 hours.

As used herein with regard to the biologically active substances, the term "aryl" is meant to include unsubstituted phenyl, phenyl substituted with one or more substituents such as lower alkyl, lower alkoxy, amino, lower alkanoyl, carboxy, carboxy, lower alkyl, halo, nitro, trifluoromethyl, substituted amino, sulfonyl, sulfamyl, aryloxy, etc., or a phenyl moiety forming part of a polynuclear structure as the A-ring of a steroid, as an aromatic ring in a tetracycline compound, etc.

The term "alkyl" as used herein with regard to alkyl amine modified inorganic support materials is meant to include straight or branched chain (containing no higher branching than a secondary carbon atom) hydrocarbon radicals having from 1 to 5 carbon atoms.

The term "lower" as used herein is meant to include substituent groups having up to 7 carbon atoms.

EXAMPLE 1

A quantity of porous 96 percent silica glass (550 A or 185 A pore size) 40–80 mesh was boiled in a 5% nitric acid solution 5 ml/gram of glass for 5 hours. The acid decanted and the glass dried at 100° C. for 4 hours. The glass was placed in 100% (by weight) of α-aminopropyltriethoxysilane solution, pH 3.5, 5 ml. per gram of glass, and mixed for 22 hours at 75° C. The solution was then decanted and the glass washed with distilled water then dried overnight at 100° C. For each gram of glass, 10 ml. of a chloroform solution was added containing 100 mg. p-nitro benzoylchloride and 50 mg. triethylamine and refluxed for 1 hour. The solution was decanted and the glass washed 3 times with chloroform, then dried for 30 minutes at 80° C. The glass was then added to to a 1% aqueous sodium dithionite solution 10 ml. per gram of glass and refluxed for 30 minutes. The solution decanted and the arylamine glass washed thoroughly with distilled water.

The arylamine glass was added to a solution of 2 NHCl at 0° C. 10 ml. per gram of glass was added and the reaction was continued at O° C. for 20 minutes under vacuum. The activated glass was rapidly washed with 1% sulfamic acid, 4° C. followed by distilled water at 4° C. The glass as a wet cake was rapidly added to a solution of L-isoproterenol (50 mg. in 10 ml. phosphate buffer 0.1 M pH 7.5). The reaction continued for 10 minutes at O° C. The supernatant was then filtered off and the isoproterenol-glass washed with 3 liters of 0.1 N HCl. The isoproterenol-glass was filtered essentially dry in a scintered glass funnel. Just enough distilled water was added to the isoproterenol-glass to obtain a wet cake. To this slurry was added as a powder 1-10 mg. of sodium dithionite and the slurry mixed well until the color change indicating the azo bond reduction was homogenous. The glass was vacuumed dry collecting the effluent. The glass was then washed twice with 10 ml. of 4° C. 0.01 M HCl. The total effluent was collected and immediately lypholized.

Purification of the 6-amino-isoproterenol from the salts present was accomplished by extracting the 6-amino-isoproterenol from the lypholized solid with absolute methanol at 0° C. The amino-isoproterenol was recovered by evaporation of the methanol. Purity was determined on thin layer silica plates in butanol: acetic acid: $H_2O$ (25: 4: 10). Nuclear magnetic resonance studies showed that an amino group had been incorporated at the six position.

EXAMPLE 2

Following the procedure of Example 1 L-epinephrine and L-norepinephrine were covalently coupled to the aryl amine glass. Synthesis and purification of the 6-amino derivatives of these agents was accomplished by an identical procedure as Example 1. The 6-amino-catecholamines have a greatly prolonged biological half-life. For example, in a test on increasing the force of isolated cardiac muscle contraction, the 6-amino-epinephrine had a duration of action in excess of 17 fold greater than that seen with epinephrine. Similar results are obtained with 6-amino-isoproterenol and 6-amino-norepinephrine.

EXAMPLE 3

Following the procedure of Example 1, D,L propranolol was covalently coupled to the arylamine glass. The coupling reaction for propranolol is much slower than for the isoproterenolin Example 1. The reaction was continued overnight at 0°-9° C. The propranolol-glass was then washed with 3 liters of 0.1 N HCl. Azo bond reduction with dithionite was accomplished following the procedure of Example 1.

Purification of the amino-propranolol was accomplished by methanol extraction. This compound showed beta adrenergic blocking activity.

EXAMPLE 4

Following the procedure of Example 1 insulin was covalently coupled to arylamine glass. The coupling reaction was continued for 4 hours at O° C. The insulin glass was then washed was 5 liters of acetate buffer 0.1M pH 4.1. The amino substituted insulin was synthesized by the dithionite-azo bond reduction procedure for isoproterenol in Example 1. The collected effluent containing the amino-insulin was added to dialysis tubing and dialyzed against distilled water for 24 hours at 4° C. with 3 volume changes. The dialysate was recovered and lypholyzed. Recoveries were monitored by using trace amounts of $I^{125}$ insulin.

EXAMPLE 5

Following the procedure of Example 1 17-beta-estradiol was convalently coupled to the arylamine glass. 20 mg. of 17-bets-estradiol was suspended in 10 ml. of phosphate buffer 0.1 M pH 8.0, to which the diazonium glass beads were added and the reaction continued for 24 hours at 0° to 4° C. The 17-beta-estradiol glass was washed with 3 liters of aboslute methanolol. The estradiol glass was air dried and resuspended in carbonate buffer 0.0 M pH 9.0 to make a glass slurry. 2 mg. sodium dithionite was added to the slurry and mixed until the color reduction was homogenous. The glass was vacuumed dry and washed twice with 10 ml. of the buffer. The effluent was collected and lypholized. The amino-17-beta-estradiol was purified by resuspending the lypholized powder in distilled water leaving the purified amino-estridiol as a precipitate. Other combinations of methanol and water extractions were equally as effective due to the large solubility differences in these solvents.

EXAMPLE 6

The amino derivatives of dopamine and L-dopa were synthesized by the procedure of Example 1. Amino histamine, amino serotonin and amino-tri-iodothyronine were prepared following the procedure of Example 3.

Amino-cocaine, amino morphine and amino atropine wer prepared by the procedure of Example 6.

EXAMPLE 7

1 gram of para amino benzoic acid was added to 25 ml. of 0.5 N HCl at 0° C. 650 mg. of sodium nitrite was added with continued mixing for 5 minutes at O° C.

Urea was the added to the reaction to consume excess nitrous acid. The loss of nitrous acid was followed with starch-iodide paper. This solution was slowly added to 2 grams of isoproterenol in 30 ml. of phosphate buffer 0.1 M, pH 7.4 and the reaction continued for 30 minutes at 0° C.

The purification of the amino substituted compounds can be accomplished by different methods.

Alternate I

By ion exchange chromatograph the benzoic-azk-compound complex can be purified free of contaiminating free drugs, urea, etc. The benzoyl-azo-drug can then be treated with 0.5 M aqueous sodium dithionite and the amino substituted compound purified from the regenerated para amino benzoic acid by perparative or ion exchange chromatography.

Alternate II

The formed benzoic-azo-drug complex was without further purification, treated with 0.5 M aqueous sodium dithionite and the produced amino substituted compound purified free of contaminant by preparative or ion exchange chromatography.

EXAMPLE 8

6-[p-nitrophenylazo]-epinephrine was synthesized by reacting p-nitroaniline (handle with care - extremely toxic) (221 mg.) in 4 ml. 1N HCl at 5° C. with 110 mt. $NaNO_2$ for 2 minutes. Exactly 0.8 ml. of 1 N NaOH was added to reach a pH of 7.0. This solution was then immediately added to 146 mg. L-epinephrine in 20 ml. phosphate buffer 0.1 M pH 7.4, containing $^{14}C$-epinephrine. This reaction was continued for 10 minutes, then the entire mixture lyophilized. The product 6-[p-nitrophenylazol]-epinephrine can be easily separated from epinephrine, p-nitro aniline, and other products using silica gel TLC plates in butanol: acetic acid: $H_1O$ (66: 17: 17). The 6-[p-nitrophenylazo]-epinephrine was purified utilizing a neutral alumina column (4 × 60 cm) eluting with butanol : acetic acid : $H_2O$ (66: 17: 17).

The purified 6-[p-nitrophenylazo]-epinephrine is soluble in methanol but only slightly soluble in $H_2O$.

The 6-[p-nitrophenylazo]-epinephrine may be used to prepare 6-$NH_2$ epinephrine employing the dithionite reduction procedure using the procedures of Example 7. The p-nitro-aniline forms a bright yellow precipitate and can be easily separated as the product compound 6-$NH_2$-epinephrine remains in solution.

The compound 6-[p-nitrophenylazo]-epinephrine is very active on isolated cat hearts with the dose response curve shifted slightly to the left of L-epinephrine. The duration of activity is also prolonged as with 6-$NH_2$-epinephrine.

I claim:
1. Amino-propranolol.

* * * * *